US009827042B2

(12) United States Patent
Sobotka

(10) Patent No.: US 9,827,042 B2
(45) Date of Patent: Nov. 28, 2017

(54) RENAL NEUROMODULATION METHODS AND DEVICES FOR TREATMENT OF POLYCYSTIC KIDNEY DISEASE

(71) Applicant: Medtronic Ardian Luxembourg S.a.r.l., Luxembourg (LU)

(72) Inventor: Paul A. Sobotka, West St. Paul, MN (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 14/852,213

(22) Filed: Sep. 11, 2015

(65) Prior Publication Data

US 2015/0374437 A1    Dec. 31, 2015

Related U.S. Application Data

(62) Division of application No. 13/691,594, filed on Nov. 30, 2012, now Pat. No. 9,192,766.
(Continued)

(51) Int. Cl.
*A61B 18/00* (2006.01)
*A61B 18/14* (2006.01)
(Continued)

(52) U.S. Cl.
CPC .......... *A61B 18/1492* (2013.01); *A61B 18/02* (2013.01); *A61F 7/12* (2013.01);
(Continued)

(58) Field of Classification Search
CPC .......... A61B 18/02; A61B 2018/00404; A61B 2018/00434; A61B 2018/00511;
(Continued)

(56) References Cited

U.S. PATENT DOCUMENTS 4,602,624 A    7/1986 Naples et al.
4,649,936 A    3/1987 Ungar et al.
(Continued)

FOREIGN PATENT DOCUMENTS

CN    103096826    5/2013
EP    0737487    10/1996
(Continued)

OTHER PUBLICATIONS

Allen, E.V., Sympathectomy for essential hypertension, Circulation, 1952, 6:131-140.
(Continued)

*Primary Examiner* — Kevin C Sirmons
*Assistant Examiner* — Deanna K Hall

(57) ABSTRACT

Methods for treating polycystic kidney disease with therapeutic renal neuromodulation and associated systems and methods are disclosed herein. One aspect of the present technology is directed to methods that at least partially inhibit sympathetic neural activity in nerves proximate a renal artery of a kidney of a patient. One or more measurable physiological parameter corresponding to the polycystic kidney disease can thereby be reduced. Moreover, central sympathetic drive in the patient can be reduced in a manner that treats the patient for the polycystic kidney disease. Renal sympathetic nerve activity can be modulated along the afferent and/or efferent pathway. The modulation can be achieved, for example, using an intravascularly positioned catheter carrying a neuromodulation assembly, e.g., a neuromodulation assembly configured to cryotherapeutically cool the renal nerve or to deliver an energy field to the renal nerve.

19 Claims, 7 Drawing Sheets

Related U.S. Application Data

(60) Provisional application No. 61/566,574, filed on Dec. 2, 2011.

(51) Int. Cl.
  *A61N 1/36* (2006.01)
  *A61N 5/00* (2006.01)
  *A61F 7/12* (2006.01)
  *A61B 18/02* (2006.01)

(52) U.S. Cl.
  CPC ......... *A61N 1/36053* (2013.01); *A61N 5/00* (2013.01); *A61B 2018/00404* (2013.01); *A61B 2018/00434* (2013.01); *A61B 2018/00511* (2013.01); *A61B 2018/0212* (2013.01); *A61F 2007/126* (2013.01); *A61N 1/36017* (2013.01)

(58) Field of Classification Search
  CPC .............. A61B 2018/0212; A61F 7/12; A61N 1/36053; A61N 5/00; A61N 1/3605; A61N 1/36057
  See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,037,391 A | 8/1991 | Hammerslag et al. |
| 5,170,803 A | 12/1992 | Henson et al. |
| 5,203,772 A | 4/1993 | Hammerslag et al. |
| 5,300,068 A | 4/1994 | Rosar et al. |
| 5,322,064 A | 6/1994 | Lundquist et al. |
| 5,358,514 A | 10/1994 | Schulman et al. |
| 5,368,591 A | 11/1994 | Lennox et al. |
| 5,415,633 A | 5/1995 | Lazarus et al. |
| 5,423,744 A | 6/1995 | Gencheff et al. |
| 5,425,364 A | 6/1995 | Imran |
| 5,437,288 A | 8/1995 | Schwartz et al. |
| 5,457,109 A | 10/1995 | Antonucci et al. |
| 5,484,400 A | 1/1996 | Edwards et al. |
| 5,487,757 A | 1/1996 | Truckai et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,658,278 A | 8/1997 | Imran et al. |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,766,167 A | 6/1998 | Eggers et al. |
| 5,772,590 A | 6/1998 | Webster, Jr. |
| 5,800,432 A | 9/1998 | Swanson |
| 5,843,152 A | 12/1998 | Tu et al. |
| 5,860,974 A | 1/1999 | Abele |
| 5,865,787 A | 2/1999 | Shapland et al. |
| 5,893,885 A | 4/1999 | Webster et al. |
| 5,899,898 A | 5/1999 | Arless et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,106,518 A | 8/2000 | Wittenberger et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,425,867 B1 | 7/2002 | Vaezy et al. |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,887,235 B2 | 5/2005 | O'Connor et al. |
| 6,893,436 B2 | 5/2005 | Woodard et al. |
| 6,939,346 B2 | 9/2005 | Kannenberg et al. |
| 6,978,174 B2 | 12/2005 | Gelfand et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,728,075 B2 | 5/2014 | Wu et al. |
| 9,486,243 B2 | 11/2016 | Eskuri |
| 2002/0065515 A1 | 5/2002 | Falwell et al. |
| 2002/0065542 A1 | 5/2002 | Lax et al. |
| 2002/0087208 A1 | 7/2002 | Koblish et al. |
| 2002/0107515 A1 | 8/2002 | Edwards et al. |
| 2002/0128662 A1 | 9/2002 | Brock et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2002/0198520 A1 | 12/2002 | Coen et al. |
| 2003/0050635 A1 | 3/2003 | Truckai et al. |
| 2003/0050681 A1 | 3/2003 | Pianca et al. |
| 2003/0055422 A1 | 3/2003 | Lesh |
| 2003/0060858 A1 | 3/2003 | Kieval et al. |
| 2003/0074039 A1 | 4/2003 | Puskas |
| 2003/0078644 A1 | 4/2003 | Phan |
| 2003/0109778 A1 | 6/2003 | Rashidi |
| 2003/0125720 A1 | 7/2003 | Woodard et al. |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0212394 A1 | 11/2003 | Pearson et al. |

(56) References Cited

U.S. PATENT DOCUMENTS

| | | | |
|---|---|---|---|
| 2003/0216792 A1 | 11/2003 | Levin et al. | |
| 2003/0229340 A1 | 12/2003 | Sherry et al. | |
| 2003/0233099 A1 | 12/2003 | Danaek et al. | |
| 2004/0010289 A1 | 1/2004 | Biggs et al. | |
| 2004/0073141 A1 | 4/2004 | Hartly et al. | |
| 2004/0167509 A1 | 8/2004 | Taimisto | |
| 2004/0215186 A1 | 10/2004 | Cornelius et al. | |
| 2005/0004644 A1 | 1/2005 | Kelsch et al. | |
| 2005/0080409 A1 | 4/2005 | Young et al. | |
| 2005/0096647 A1 | 5/2005 | Steinke et al. | |
| 2005/0187455 A1 | 8/2005 | Rashidi | |
| 2005/0187579 A1 | 8/2005 | Danek et al. | |
| 2005/0228460 A1 | 10/2005 | Levin et al. | |
| 2005/0240229 A1 | 10/2005 | Whitehurst et al. | |
| 2005/0267010 A1 | 12/2005 | Goodson et al. | |
| 2005/0288730 A1 | 12/2005 | Deem et al. | |
| 2006/0079943 A1 | 4/2006 | Narciso | |
| 2006/0085054 A1 | 4/2006 | Zikorus et al. | |
| 2006/0095029 A1 | 5/2006 | Young et al. | |
| 2006/0100618 A1 | 5/2006 | Chan et al. | |
| 2006/0206150 A1 | 9/2006 | Demarais et al. | |
| 2006/0212076 A1 | 9/2006 | Demarais et al. | |
| 2006/0271111 A1 | 11/2006 | Demarais et al. | |
| 2007/0066878 A1 | 3/2007 | Worley et al. | |
| 2007/0129720 A1 | 6/2007 | Demarais et al. | |
| 2007/0135875 A1 | 6/2007 | Demarais et al. | |
| 2007/0156131 A1 | 7/2007 | Datta | |
| 2007/0173891 A1 | 7/2007 | Buras | |
| 2007/0265687 A1 | 11/2007 | Deem et al. | |
| 2008/0255642 A1 | 10/2008 | Zarins et al. | |
| 2008/0319513 A1 | 12/2008 | Pu et al. | |
| 2009/0024195 A1 | 1/2009 | Rezai et al. | |
| 2009/0036948 A1 | 2/2009 | Levin et al. | |
| 2009/0062873 A1 | 3/2009 | Wu et al. | |
| 2009/0076409 A1 | 3/2009 | Wu et al. | |
| 2010/0119482 A1 | 5/2010 | Yun et al. | |
| 2010/0137700 A1 | 6/2010 | Passman et al. | |
| 2010/0137860 A1 | 6/2010 | Demarais et al. | |
| 2010/0137952 A1 | 6/2010 | Demarais et al. | |
| 2010/0168731 A1 | 7/2010 | Wu et al. | |
| 2010/0168739 A1 | 7/2010 | Wu et al. | |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2010/0286684 A1 | 11/2010 | Hata et al. | |
| 2010/0286734 A1 | 11/2010 | Yun et al. | |
| 2011/0052718 A1 | 3/2011 | Rangel | |
| 2011/0144468 A1 | 6/2011 | Boggs et al. | |
| 2011/0264011 A1* | 10/2011 | Wu | A61F 5/0013 601/2 |
| 2011/0264075 A1 | 10/2011 | Leung et al. | |
| 2012/0116382 A1 | 5/2012 | Ku et al. | |
| 2012/0130289 A1 | 5/2012 | Demarais et al. | |
| 2012/0130345 A1 | 5/2012 | Levin et al. | |
| 2012/0136350 A1 | 5/2012 | Goshgarian et al. | |
| 2012/0150267 A1 | 6/2012 | Buckley et al. | |
| 2012/0172837 A1 | 7/2012 | Demarais et al. | |
| 2013/0144251 A1 | 6/2013 | Sobotka | |
| 2015/0051594 A1 | 2/2015 | Sobotka | |

FOREIGN PATENT DOCUMENTS

| | | |
|---|---|---|
| EP | 2563255 | 3/2013 |
| WO | WO-9407446 | 4/1994 |
| WO | WO-9525472 | 9/1995 |
| WO | WO-9531142 | 11/1995 |
| WO | WO-9736548 | 10/1997 |
| WO | WO9842403 | 10/1998 |
| WO | WO-9900060 | 1/1999 |
| WO | WO-0122897 | 4/2001 |
| WO | WO-0170114 | 9/2001 |
| WO | WO-03022167 | 3/2003 |
| WO | WO-03/082080 | 10/2003 |
| WO | WO-2005030072 | 4/2005 |
| WO | WO--2005041748 | 5/2005 |
| WO | WO-2005/110528 | 11/2005 |
| WO | WO-2006041881 | 4/2006 |
| WO | WO2006086152 | 8/2006 |
| WO | WO-2006105121 | 10/2006 |
| WO | WO-2007008954 | 1/2007 |
| WO | WO-2007078997 | 7/2007 |
| WO | WO-2008049084 | 4/2008 |
| WO | WO2009086007 | 7/2009 |
| WO | WO2011139589 | 11/2011 |
| WO | WO-2012019156 | 2/2012 |
| WO | WO2012054906 | 4/2012 |
| WO | WO-2013134548 | 9/2013 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.

Schlaich, M.P. et al., "Renal Denervation as a Therapeutic Approach for Hypertension: Novel Implications for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.

(56) References Cited

OTHER PUBLICATIONS

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
International Search Report and Written Opinion for International App. No. PCT/US13/29690, Mailed May 9, 2013, 10 pages.
Barbieri, R. et al., "Treatment of polycystic ovary syndrome in adults," Wolters Kluwer Health, 2012, 11 pgs. <http://www.uptodate.com>.
Barria A. et al., "Ovarian Steroidal Response to Gonadotropins and β-Adrenergic Stimulation Is Enhanced in Polycystic Ovary Syndrome: Role of Sympathetic Innervation." Endocrinology, 1993, vol. 133, No. 6, 8 pages.
Diamanti-Kandarakis, E. et al., "The Role of Genes and Environment in the Etiology of PCOS." Endocrine, vol. 30, No. 1, Aug. 2006, pp. 19-26.
Ehrmann, David, "Polycystic Ovary Syndrome," The New England Journal of Medicine, vol. 352, 2005, 1223-36.
Esler M. et al., "Catheter-Based Renal Denervation Reduces Total Body and Renal Noradrenaline Spillover and Blood Pressure in Resistant," Hypertension, J Hypertens vol. 27, 2009, 1 page.
Fauser et al. "Consensus on women's health aspects of polycystic ovary syndrome (PCOS): the Amsterdam ESHRE/ASRM-Sponsored 3rd PCOS Consensus Workshop Group." Fertility and sterility 2012; 97: 36 pages.
Hendriks et al. "Why does ovarian surgery in PCOS help? Insight into the endocrine implications of ovarian surgery for ovulation induction in polycystic ovary syndrome." Human reproduction update, 2007; 13: 16 pages.
Himelein et al. "Polycystic ovary syndrome and mental health: A review." Obstet Gynecol. Surv. 2006; 61(11): 723-732.
Lansdown et al. "The Sympathetic Nervous System in Polycystic Ovary Syndrome: a novel therapeutic target?" Clinical endocrinology, 2012, 28 pages.
Lembo et al., "A lesson from polycystic ovarian syndrome: untangling the role of renal sympathetic nervous system on hypertension and insulin resistance." J Hypertens, 2011; 29: 2 pages.
Nakamura Y., "Treatment of Polycystic Ovary Syndrome: An Overview." Hormone Research 1990; 33: 1 page.
Schlaich et al., "Renal denervation: a potential new treatment modality for polycystic ovary syndrome?" J Hypertens 2011; 29: 991-6.
Schlaich MP et al., "A Novel Catheter Based Approach to Denervate the Human Kidney Reduces Blood Pressure and Muscle Sympathetic Nerve Activity in a Patient with End Stage Renal Disease and Hypertension." J Hypertens 2009; 27: 1 page.
Schlaich MP et al., Renal sympathetic-nerve ablation for uncontrolled hypertension. N Engl J Med 2009; 361: 932-4.
Stener-Victorin et al. "Low-frequency electroacupuncture and physical exercise decrease high muscle sympathetic nerve activity in polycystic ovary syndrome." Am J Physiol Regul Integr Comp Physiol, 2009; 297: R387-95.
Sverrisdottir et al., "Is Polycystic Ovary Syndrome Associated with High Sympathetic Nerve Activity and Size at Birth?" American Journal of Physiology—Endocrinology and Metabolism. Jan. 15, 2008, vol. 294, p. E576-E581.
European Search Report for European Application No. 13159256, Date Mailed: Oct. 17, 2013, 6 pages.

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.

(56) References Cited

OTHER PUBLICATIONS

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Interv Cardiac Electrophysiol, 2:285-292 (1998).

Final Office Action, U.S. Appl. No. 12/827,700, Mailed on Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, Col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." *Am. J. Roentgenol*,174: 1592-1594 (2000).

Han, Y.-M, et al., "Renal artery ebolization with diluted hot contrast medium: An experimental study." J Vasc Interv Radiol, 12: 862-868 (2001).

Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:11-17-11-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Solis-Herruzo et al., "Effects of lumbar sympathetic block on kidney function in cirrhotic patients with hepatorenal syndrome," J. Hepatol. 5 (1987), pp. 167-173.

(56) References Cited

OTHER PUBLICATIONS

Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." Pace, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Bajwa et al., "Pain management in polycystic kidney disease." Kidney Int 2001; 60: 1631-44.
Cerasola et al. "Role of renin-angiotensin-aldosterone system and of sympathetic activity in arterial hypertension associated with autosomal dominant polycystic kidney disease." Contrib Nephrol 1997; 122: 22-27.
Chapman et al., "Course and treatment of autosomal dominant polycystic kidney disease." UpToDate, 2012, 18 pages. <www.uptodate.com>.
Dunn et al., "Laparoscopic Nephrectomy in Patients With End-Stage Renal Disease and Autosomal Dominant Polycystic Kydney Disesase." American Journal of Kidney Diseases, vol. 35, No. 4, 2000, 6 pages.
Gattone II, V. H. et al. "Contribution of Renal Innervation to Hypertension in Polycystic Kidney Disease in the Rat." Exp Biol Med (Maywood) 2008. doi:0802-RM-54 [pii] 10.3181/0802-RM-54.
Greenwell et al., "The outcome of renal denervation for managing loin pain haematuria syndrome." BJU International, 2004, 93, 4 pages.

Helal et al., Glomerular hyperfiltration and renal progression in children with autosomal dominant polycystic kidney disease. Clin J Am Soc Nephrol 2011; 6: 2439-43.
Kelleher et al., "Characteristics of Hypertension in Young Adults With Autosomal Dominant Polycystic Kidney Disease Compared With the General U.S. Population." AJH, 2004 17, 6 pages.
Klein et al., "Sympathetic Activity Is Increased in Polycystic Kidney Disease and Is Associated with Hypertension." J Am Soc Nephrol, 2001, vol. 12, 7 pages.
Luippold et al., "Chronic renal denervation prevents glomerular hyperfiltration in diabetic rats." Nephrol Dial Transplant 2004; 19: 342-7.
Schrier et al., "Cardiac and Renal Effects of Standard Versus Rigorous Blood Pressure Control in Autosomal-Dominant Polycystic Kidney Disease: Results of a Seven-Year Prospective Randomized Study." J Am Soc Nephrol, 2002, 13, 7 pages.
Shetty et al., "Percutaneous transluminal renal denervation: A potential treatment option for polycystic kidney disease-related pain?" International Journal of Cardiology, 2012, 2 pages.
Torres et al., "Autosomal dominant polycystic kidney disease." The Lancet 2007; 369: 1287-301.
Wong H. et al., "Patients with autosomal dominant polycystic kidney disease hyperfiltrate early in their disease," Am J Kidney Dis, vol. 43, 2004, 624-8.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005, (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper et al., "Design and Implementation of a New Computerized System for Intraoperative Cardiac Mapping." Journal of Applied Physiology, 1991, vol. 71, No. 4, pp. 1529-1539.
Prochnau, Dirk et al., Catheter-based renal denervation for drug-resistant hypertension by using a standard electrophysiology catheter; Euro Intervention 2012, vol. 7, pp. 1077-1080.

(56) References Cited

OTHER PUBLICATIONS

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 60/852,787, filed Oct. 18, 2006, 112 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European Patent No. 2465470, Granted Oct. 28, 2015, Date of Opposition Jul. 27, 2016, 34 pp.
U.S. Appl. No. 11/363,867, filed Feb. 27, 2006, 70 pp.
U.S. Appl. No. 60/813,589, filed Dec. 29, 2005, 62 pp.
Ureter, https://en.wikipedia.org/wiki/Ureter, Jun. 2016, 6 pp.
Stener-Victorin, et al., "Acupuncture in Polycystic Ovary Syndrome: Current Experimental and Clinical Evidence", J. Neuroendocrinol, 2008, vol. 20 (3), pp. 290-298.
Lara, et al., "Activation of ovarian sympathetic nerves in polycystic ovary syndrome." Endocrinology 1993, 133, 6 pages.

\* cited by examiner

*Arterial Vasculature*

*Venous Vasculature*

RENAL NEUROMODULATION METHODS AND DEVICES FOR TREATMENT OF POLYCYSTIC KIDNEY DISEASE

RELATED APPLICATIONS INCORPORATED BY REFERENCE

The present application is a Division of and claims priority to U.S. patent application Ser. No. 13/691,594 filed Nov. 30, 2012, now allowed, which claims priority to U.S. Provisional Patent Application No. 61/566,574, filed Dec. 2, 2011, entitled "TREATMENT OF POLYCYSTIC KIDNEY DISEASE USING RENAL NEUROMODULATION," both of which are incorporated herein in their entirety by reference.

TECHNICAL FIELD

The present technology relates generally to polycystic kidney disease and related conditions. In particular, several embodiments are directed to treatment of polycystic kidney disease and related conditions using renal neuromodulation and associated systems and methods.

BACKGROUND

Polycystic kidney disease (PKD) is a genetically inherited disease and one of the leading causes of end-stage renal disease. PKD can be characterized by the presence of multiple, fluid-filled cysts in one or both kidneys, resulting in massive enlargement of the kidneys. Disease progression can lead to reduction in renal function and eventual kidney failure can require dialysis and possible kidney transplantation in up to 50% of patients. Autosomal dominant PKD (ADPKD) is the most commonly inherited form of the disease that can affect about 1 in 400 to 1 in 1000 people worldwide. ADPKD typically progresses to end-stage renal disease in the 4th to 6th decades of life. Additional clinical manifestations of ADPKD can include hypertension, back and side pain, cerebral aneurysms, hepatic cysts, pancreatic cysts, cardiac valve disease (especially mitral valve prolapse), urinary tract infections, hematuria, kidney stones, colonic diverticula, and aortic root dilatation. Most prescribed treatments address specific manifestations of PKD and do not address underlying causes of the disease and/or have not been proven to prevent or delay decline of renal function. For example, over-the-counter pain medications (e.g., NSAIDs, acetaminophen) or prescribed narcotics or other pain medications are used to control pain symptoms, and anti-hypertensive medications are prescribed to control blood pressure.

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. As examples, radiotracer dilution has demonstrated increased renal norepinephrine (NE) spillover rates in patients with essential hypertension, and elevated sympathetic nervous system activity has been shown to be present in ADPKD.

Sympathetic nerves of the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone as well as likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II calcium channel blockers and vasodilators (to counteract peripheral vasoconstriction caused by increased sympathetic drive), aldosterone blockers (to block the actions of increased aldosterone released from activation of the renin-angiotensin-aldosterone system), and aldosterone activation consequent to renin release), and diuretics (intended to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Figure 1:
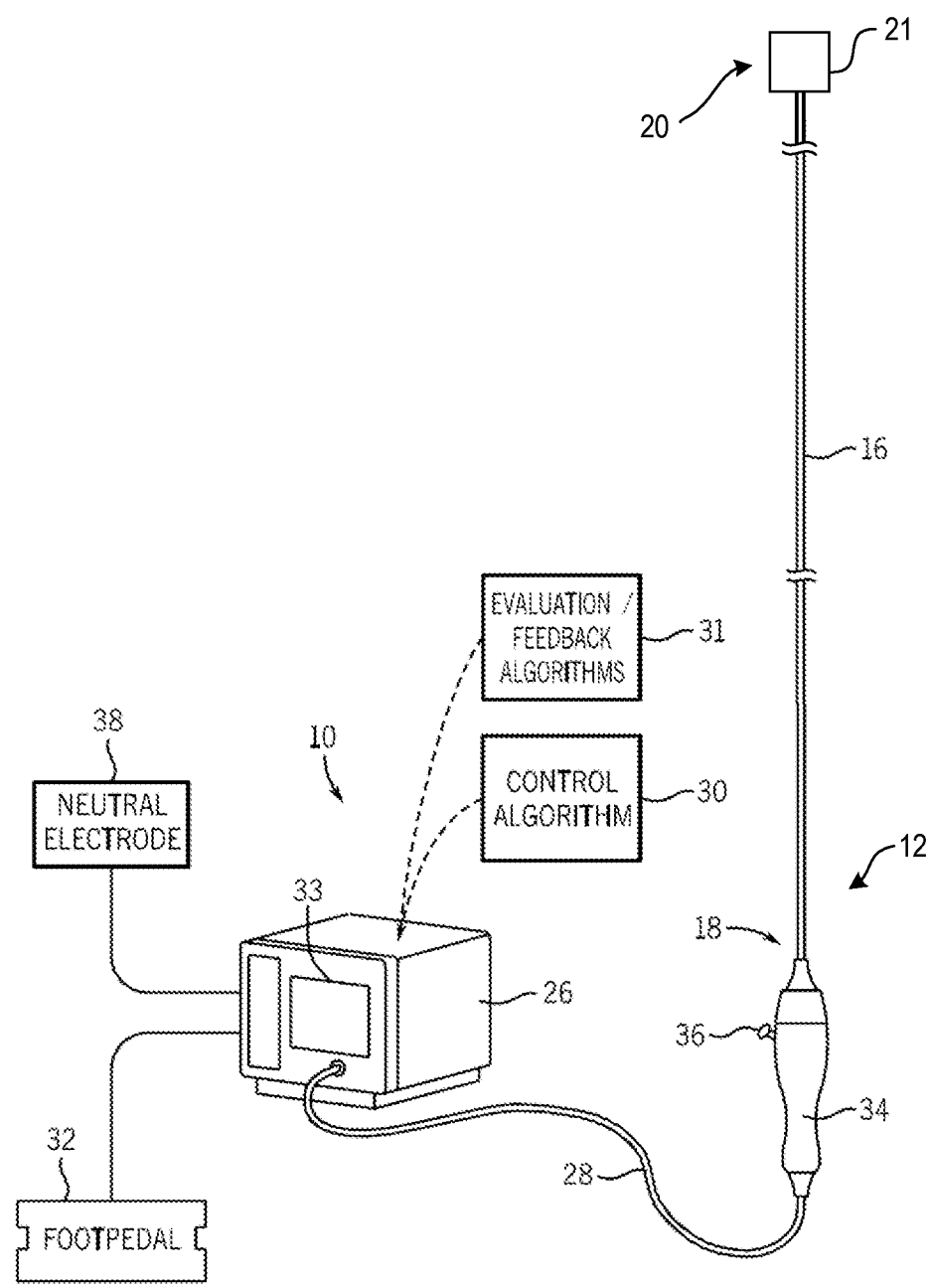
FIG. 1 illustrates an intravascular neuromodulation system configured in accordance with an embodiment of the present technology.

The present technology is directed to apparatuses, systems, and methods for treating PKD and related conditions using renal neuromodulation. For example, some embodiments include performing therapeutically-effective renal neuromodulation on a patient diagnosed with PKD. As discussed in greater detail below, renal neuromodulation can include rendering neural fibers inert, inactive, or otherwise completely or partially reduced in function. This result can be electrically-induced, thermally-induced, or induced by another mechanism during a renal neuromodulation procedure, e.g., a procedure including percutaneous transluminal intravascular access.

Specific details of several embodiments of the technology are described below with reference to FIGS. 1-7B. Although many of the embodiments are described below with respect to devices, systems, and methods for intravascular modulation of renal nerves using cryotherapeutic and electrode-based approaches, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-7B.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. Polycystic Kidney Disease

PKD can be characterized by the presence of numerous cysts in the kidneys and/or other clinical manifestations associated with the disease. The two major forms (i.e., autosomal dominant, autosomal recessive) of the disease are distinguished by their patterns of inheritance. In addition to cysts in the kidneys, the clinical presentation of PKD can include kidney enlargement, reduction in kidney function, kidney failure, pain in the back and sides, headaches, urinary tract infections, hematuria, liver cysts, pancreatic cysts, abnormal heart valves, hypertension, kidney stones, aneurysms, and diverticulosis. ADPKD can be inherited via genetic mutations in the PKD-1, PKD-2, and PKD-3 genes. Autosomal recessive PKD (ARPKD), a less common genetically inherited disease, is caused by mutations in the PKHD1 gene. Accordingly, patients with a positive family history and/or clinical symptoms may be screened using imaging (e.g. ultrasound, CT scan, MRI) and/or genetic screening showing mutations in the PKD-1, PKD-2, PKD-3 or PKHD1 genes. Additional diagnosis testing can be performed, for example, to assess a patient's heart valve condition, blood pressure, and measure of perceived pain. In another embodiment, PKD patients or patients suspected of having PKD can be assessed for markers of renal injury, for example, serum BUN levels, serum creatinine levels, serum cystatin C levels, proteinuria levels, neutrophil gelatinase-associated lipocalin (NGAL) levels, and kidney injury molecule-1 (Kim-1) levels. In further embodiments, PKD patients or patients suspected of having PKD can be assessed for elevated sympathetic nerve activity, including establishing measurements for markers of elevated sympathetic nerve activity, including for example, muscle sympathetic nerve activity (MSNA), spillover (e.g., renal or total body) plasma norepinephrine levels, and heart rate variability.

II. Renal Neuromodulation

Renal neuromodulation is the partial or complete incapacitation or other effective disruption of nerves innervating the kidneys. In particular, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks).

Intravascular devices that reduce sympathetic nerve activity by applying, for example, RF energy to a target site in the renal artery have recently been shown to reduce blood pressure in patients with treatment-resistant hypertension. The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent renin-angiotensin-aldosterone system (RAAS) activation) and sodium retention and decreased renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure).

Various techniques can be used to partially or completely incapacitate neural pathways, such as those innervating the kidney. The purposeful application of energy (e.g., electrical energy, thermal energy) to tissue can induce one or more desired thermal heating and/or cooling effects on localized regions along all or a portion of the renal artery and adjacent regions of the renal plexus RP, which lay intimately within or adjacent to the adventitia of the renal artery. Some embodiments of the present technology, for example, include cryotherapeutic renal neuromodulation, which can include cooling tissue at a target site in a manner that modulates neural function. The mechanisms of cryotherapeutic tissue damage include, for example, direct cell injury (e.g., necrosis), vascular injury (e.g., starving the cell from nutrients by damaging supplying blood vessels), and sub-lethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a renal artery wall such that proximate (e.g., adjacent) tissue is effectively cooled to a depth where sympathetic renal nerves reside. For example, a cooling structure can be cooled to the extent that it causes therapeutically-effective, cryogenic renal-nerve modulation. Sufficiently cooling at least a portion of a sympathetic renal nerve may slow or potentially block conduction of neural signals to produce a prolonged or permanent reduction in renal sympathetic activity.

As an alternative to or in conjunction with cryotherapeutic cooling, other suitable energy delivery techniques, such as electrode-based approaches, can be used for therapeutically-effective renal neuromodulation. For example, an energy delivery element (e.g., electrode) can be configured to deliver electrical and/or thermal energy at a treatment site. Suitable energy modalities can include, for example, radiofrequency (RF) energy (monopolar and/or bipolar), pulsed RF energy, microwave energy, ultrasound energy, high-intensity focused ultrasound (HIFU) energy, laser, optical energy, magnetic, direct heat, or other suitable energy modalities alone or in combination. Moreover, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and incorporated herein by reference in its entirety. Other suitable devices and technologies, such as cryotherapeutic devices are described in U.S. patent application Ser. No. 13/279,330, filed Oct. 23, 2011, and additional thermal devices are described in U.S. patent application Ser. No. 13/279,205, filed Oct. 21, 2011, each of which are incorporated herein by reference in their entireties.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C.

III. Methods for Treatment of Polycystic Kidney Disease

Disclosed herein are several embodiments of methods directed to treatment of PKD and related conditions using renal neuromodulation. The methods disclosed herein are expected to represent a significant improvement over conventional approaches and techniques in that they may allow for potential targeting of the cause of PKD, and provide for localized treatment and limited duration (e.g., one-time treatment) treatment regimes.

In certain embodiments, the methods provided herein comprise performing thermal ablation, thereby decreasing sympathetic renal nerve activity. In certain embodiments, thermal ablation may be repeated one or more times at various intervals until a desired sympathetic nerve activity level or another therapeutic benchmark is reached. In one embodiment, a decrease in sympathetic nerve activity may be observed via a marker of sympathetic nerve activity in PKD patients, such as decreased levels of plasma norepinephrine (noradrenaline). Other measures or markers of sympathetic nerve activity can include MSNA, sympathetic spillover, and/or heart rate variability. In another embodiment, other measurable physiological parameters or markers, such as reduction in pain level perceived by the PKD patient, improved blood pressure control, reduction in cyst size, etc., can be used to assess efficacy of the thermal ablation treatment for PKD patients.

In certain embodiments of the methods provided herein, thermal ablation results in a decrease in sympathetic nerve activity over a specific timeframe. In certain of these embodiments, sympathetic nerve activity levels are decreased over an extended timeframe, e.g., within 1 month, 2 months, 3 months, 6, months, 9 months or 12 months post-ablation.

In certain embodiments, the methods disclosed herein may comprise an additional step of measuring sympathetic nerve activity levels, and in certain of these embodiments the methods further comprise comparing the activity level to a baseline activity level. Such comparisons can be used to monitor therapeutic efficacy and to determine when and if to repeat the ablation procedure. In certain embodiments, a baseline sympathetic nerve activity level is derived from the subject undergoing treatment. For example, baseline sympathetic nerve activity level may be measured in the subject at one or more timepoints prior to thermal ablation. A baseline sympathetic nerve activity value may represent sympathetic nerve activity at a specific timepoint before thermal ablation, or it may represent an average activity level at two or more timepoints prior to thermal ablation. In certain embodiments, the baseline value is based on sympathetic nerve activity immediately prior to thermal ablation (e.g., after the subject has already been catheterized). Alternatively, a baseline value may be derived from a standard value for sympathetic nerve activity observed across the population as a whole or across a particular subpopulation. In certain embodiments, post-ablation sympathetic nerve activity levels are measured in extended timeframes post-ablation, e.g., 3 months, 6 months or 12 months post ablation.

In certain embodiments of the methods provided herein, the methods are designed to decrease sympathetic nerve activity to a target level. In these embodiments, the methods include a step of measuring sympathetic nerve activity levels post-ablation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

Renal neuromodulation may be performed on a patient diagnosed with PKD to reduce one or more measurable physiological parameters corresponding to the PKD. In some embodiments, renal neuromodulation may prevent increase of, maintain, or reduce kidney-cyst size with regard to a particular kidney cyst or an average size of some or all kidney cysts in a patient. A reduction in kidney-cyst size can be, for example, at least about 5%, 10%, or a greater amount as determined by qualitative or quantitative analysis (e.g., ultrasound) before and after (e.g., 1, 3, 6, or 12 months after) a renal neuromodulation procedure. Corresponding results may be obtained with regard to liver cysts, pancreatic cysts, and/or overall organ size of the kidney, liver, or pancreas. In addition to or instead of affecting the growth or size of one or more cysts in a patient, renal neuromodulation may efficaciously treat another measurable physiological parameter or sequela corresponding to PKD. For example, in some embodiments, renal neuromodulation may reduce the severity and/or frequency of pain, hypertension, headaches, urinary tract infections, hematuria, kidney stones, aneurysms, and/or diverticulosis. In another embodiment, renal neuromodulation may result in reduction of renal cysts and/or prevention of additional kidney cysts from forming. Furthermore, renal neuromodulation may improve markers of renal injury (e.g., serum BUN levels, serum creatinine levels, serum cystatin C levels, proteinuria levels, NGAL levels, and Kim-1 levels) or may improve renal function (e.g., slow a decline in glomerular filtration rate) in a patient, prevent end-stage renal disease, etc. These and other results may occur at various times, e.g., directly following renal neuromodulation or within about one month, three months, six months, a year, or a longer period following renal neuromodulation.

The progression of PKD may be related to sympathetic overactivity and, correspondingly, the degree of sympatho-excitation in a patient may be related to the severity of the clinical presentation of the PKD. The kidneys are strategically positioned to be both a cause (via afferent nerve fibers) and a target (via efferent sympathetic nerves) of elevated central sympathetic drive. Without being bound by theory, it is believed that the sympathetic nervous system may impact fluid retention in kidney cysts and that renal neuromodulation may treat this inappropriate fluid retention. In some embodiments, renal neuromodulation is used to reduce central sympathetic drive in a patient diagnosed with PKD in a manner that treats the patient for the PKD. For example, muscle sympathetic nerve activity can be reduced by at least about 10% in the patient within about three months after at least partially inhibiting sympathetic neural activity in nerves proximate a renal artery of the kidney. Similarly, whole body norepinephrine spillover can be reduced at least about 20% in the patient within about three months after at least partially inhibiting sympathetic neural activity in nerves proximate a renal artery of the kidney.

In one prophetic example, a patient diagnosed with PKD can be subjected to a baseline assessment indicating a first set of measurable parameters corresponding to the PKD. Such parameters can include, for example, blood pressure, sodium level, potassium level, fasting glucose level, measures of insulin sensitivity, and markers of renal damage or measures of renal function (e.g. creatinine level, estimated glomerular filtration rate, blood urea nitrogen level, creatinine clearance, cystatin-C level, NGAL levels, KIM-1 levels, presence of proteinuria or microalbuminuria, urinary albumin creatinine ratio). The patient also can be tested (e.g., using ultrasound) to determine a baseline size of one or more cysts of the kidney, liver, or pancreas. Following baseline assessment, the patient can be subjected to a renal neuromodulation procedure. Such a procedure can, for example, include any of the treatment modalities described herein or another treatment modality in accordance with the present technology. The treatment can be performed on nerves proximate one or both kidneys of the patient. Following the treatment (e.g., 1, 3, 6, or 12 months following the treatment), the patient can be subjected to a follow-up assessment. The follow-up assessment can indicate a measurable improvement in one or more physiological parameters corresponding to the PKD.

The methods described herein address the sympathetic excess that is thought to be an underlying cause of PKD or a central mechanism through which PKD manifests its multiple deleterious effects on patients. In contrast, known therapies currently prescribed for PKD patients typically address only specific manifestations of PKD. Additionally, conventional therapies require the patient to remain compliant with the treatment regimen over time. In contrast, renal neuromodulation can be a one-time treatment that would be expected to have durable benefits to inhibit the long-term disease progression and thereby achieve a favorable patient outcome.

In one embodiment, patients diagnosed with PKD can be treated with combinations of therapies for treating both primary causative modes of PKD as well as sequelae of PKD. For example, combinations of therapies can be tailored based on specific manifestations of the disease in a particular patient. In a specific example, patients having PKD and presenting hypertension can be treated with both antihypertensive drugs and renal neuromodulation. In another example, renal neuromodulation can be combined with vasopressin inhibitors (e.g., Tolvaptan), increased fluid intake, maximal inhibition of the renin-angiotensin-aldosterone system, and mTOR inhibitors.

Treatment of PKD or related conditions may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A. ADDITIONAL EXAMPLES

Example 1

Effect of Renal Neuromodulation on Hypertension

Patients selected having a baseline systolic blood pressure of 160 mm Hg or more (≥150 mm Hg for patients with type 2 diabetes) and taking three or more antihypertensive drugs, were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, $p<0.0001$), whereas they did not differ from baseline in the control group (change of 1/0 mm Hg, baseline of 178/97 mm Hg, $p=0.77$ systolic and $p=0.83$ diastolic). Between-group differences in blood pressure at 6 months were 33/11 mm Hg ($p<0.0001$). At 6 months, 41 (84%) of 49 patients who underwent renal neuromodulation had a reduction in systolic blood pressure of 10 mm Hg or more, compared with 18 (35%) of 51 control patients ($p<0.0001$).

IV. Selected Embodiments of Renal Neuromodulation Systems and Devices

FIG. 1 illustrates a renal neuromodulation system 10 configured in accordance with an embodiment of the present technology. The system 10, for example, may be used to perform therapeutically-effective renal neuromodulation on a patient diagnosed with PKD. The system 10 includes an intravascular treatment device 12 operably coupled to an energy source or console 26 (e.g., a radiofrequency energy generator, a cryotherapy console). In the embodiment shown in FIG. 1, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a neuromodulation assembly or treatment section 21 at the distal portion 20 of the shaft 16. The neuromodulation assembly 21 can include one or more electrodes or energy-delivery elements, a cryotherapeutic cooling assembly and/or a nerve monitoring device configured to be delivered to a renal blood vessel (e.g., a renal artery) in a low-profile configuration.

Upon delivery to a target treatment site within a renal blood vessel, the neuromodulation assembly 21 can be further configured to be deployed into a treatment state or arrangement for delivering energy at the treatment site and providing therapeutically-effective electrically-induced and/or thermally-induced renal neuromodulation. In some embodiments, the neuromodulation assembly 21 may be placed or transformed into the deployed state or arrangement via remote actuation, e.g., via an actuator 36, such as a knob, pin, or lever carried by the handle 34. In other embodiments, however, the neuromodulation assembly 21 may be transformed between the delivery and deployed states using other suitable mechanisms or techniques. The proximal end of the neuromodulation assembly 21 can be carried by or affixed to the distal portion 20 of the elongated shaft 16. A distal end of the neuromodulation assembly 21 may terminate with, for example, an atraumatic rounded tip or cap. Alternatively, the distal end of the neuromodulation assembly 21 may be configured to engage another element of the system 10 or treatment device 12. For example, the distal end of the neuromodulation assembly 21 may define a passageway for engaging a guide wire (not shown) for delivery of the treatment device using over-the-wire ("OTW") or rapid exchange ("RX") techniques.

The energy source or console 26 can be configured to generate a selected form and magnitude of energy for delivery to the target treatment site via the neuromodulation assembly 21. A control mechanism, such as a foot pedal 32, may be connected (e.g., pneumatically connected or electrically connected) to the energy source or console 26 to allow an operator to initiate, terminate and, optionally, adjust various operational characteristics of the energy source or console 26, including, but not limited to, power delivery. The system 10 may also include a remote control device (not shown) that can be positioned in a sterile filed and operably coupled to the neuromodulation assembly 21. The remote control device can be configured to allow for selective activation of the neuromodulation assembly 21. In other embodiments, the remote control device may be built into the handle assembly 34. The energy source 26 can be configured to deliver the treatment energy via an automated control algorithm 30 and/or under the control of the clinician. In addition, the energy source 26 may include one or more evaluation or feedback algorithms 31 to provide feedback to the clinician before, during, and/or after therapy.

The energy source 26 can further include a device or monitor that may include processing circuitry, such as a microprocessor, and a display 33. The processing circuitry may be configured to execute stored instructions relating to the control algorithm 30. The energy source 26 may be configured to communicate with the treatment device 12 (e.g., via a cable 28) to control the neuromodulation assembly and/or to send signals to or receive signals from the nerve monitoring device. The display 33 may be configured to provide indications of power levels or sensor data, such as audio, visual or other indications, or may be configured to communicate information to another device. For example, the console 26 may also be configured to be operably coupled to a catheter lab screen or system for displaying treatment information, such as nerve activity before and/or after treatment.

Figure 2:
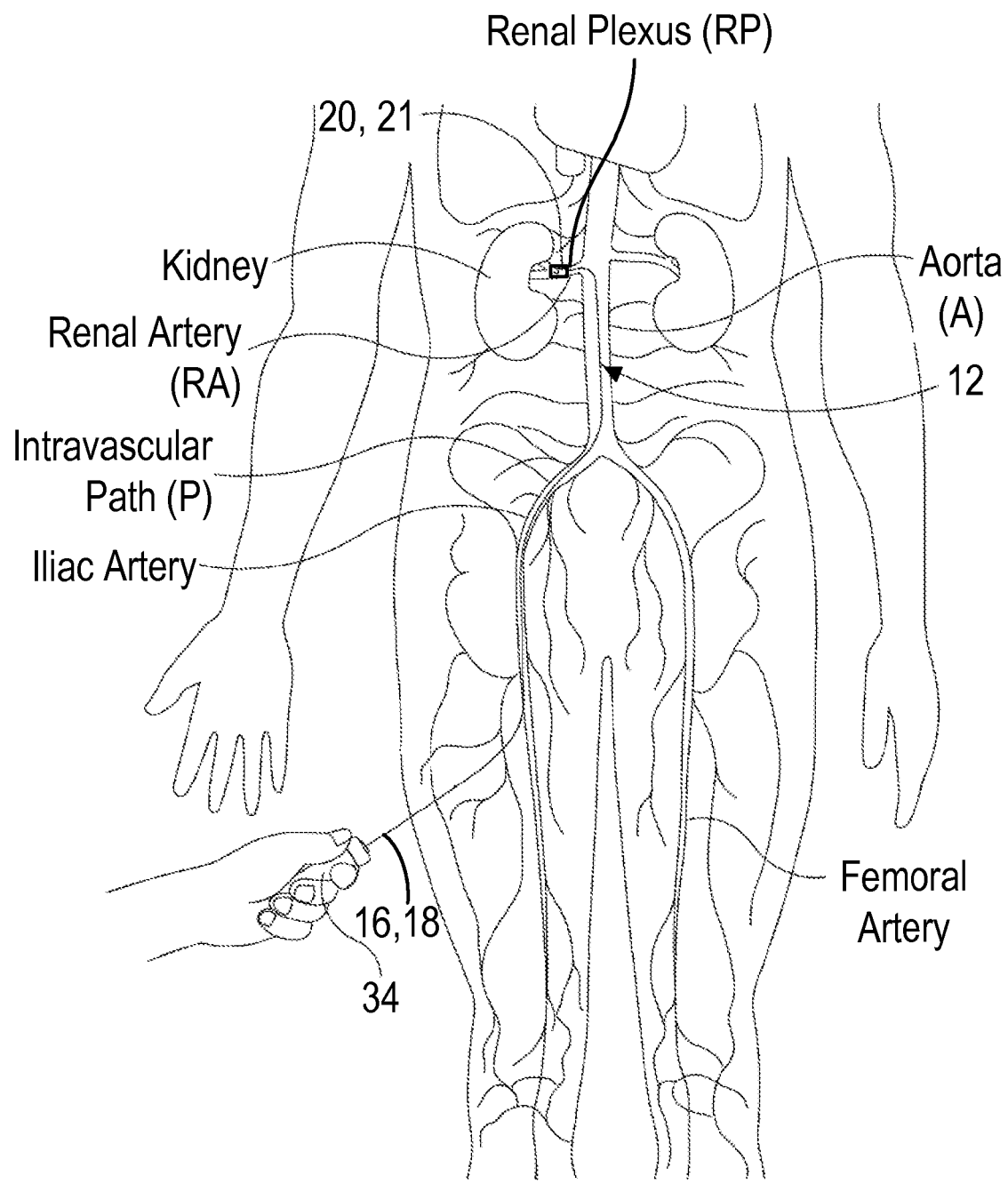
FIG. 2 illustrates modulating renal nerves with a neuromodulation system configured in accordance with an embodiment of the present technology.

FIG. 2 illustrates modulating renal nerves with an embodiment of the system 10. The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12.

After the neuromodulation assembly 21 is adequately positioned in the renal artery RA, it can be radially expanded or otherwise deployed using the handle 34 or other suitable control mechanism until the neuromodulation assembly is positioned at its target site and in stable contact with the inner wall of the renal artery RA. The purposeful application of energy from the neuromodulation assembly can then be applied to tissue to induce one or more desired neuromodulating effects on localized regions of the renal artery RA and adjacent regions of the renal plexus RP, which lay intimately within, adjacent to, or in close proximity to the adventitia of the renal artery RA. The neuromodulating effects may include denervation, thermal ablation, and non-ablative thermal alteration or damage (e.g., via sustained heating and/or resistive heating). The purposeful application of the energy may achieve neuromodulation along all or at least a portion of the renal plexus RP.

As mentioned previously, the methods disclosed herein may use a variety of suitable energy modalities, including RF energy, microwave energy, laser, optical energy, ultrasound, HIFU, magnetic energy, direct heat, cryotherapy, or a combination thereof. Alternatively or in addition to these techniques, the methods may utilize one or more non-ablative neuromodulatory techniques. For example, the methods may utilize non-ablative SNS denervation by removal of target nerves, injection of target nerves with a destructive drug or pharmaceutical compound, or treatment of the target nerves with non-ablative energy modalities. In certain embodiments, the amount of reduction of the sympathetic nerve activity may vary depending on the specific technique being used.

In certain embodiments, a neuromodulation device for use in the methods disclosed herein may combine two or more energy modalities. For example, the device may include both a hyperthermic source of ablative energy and a hypothermic source, making it capable of, for example, performing both RF ablation and cryoablation. The distal end of the treatment device may be straight (for example, a focal catheter), expandable (for example, an expanding mesh or cryoballoon), or have any other configuration (e.g., a helical coil as shown in FIG. 16 and FIG. 17). Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

Figure 3:
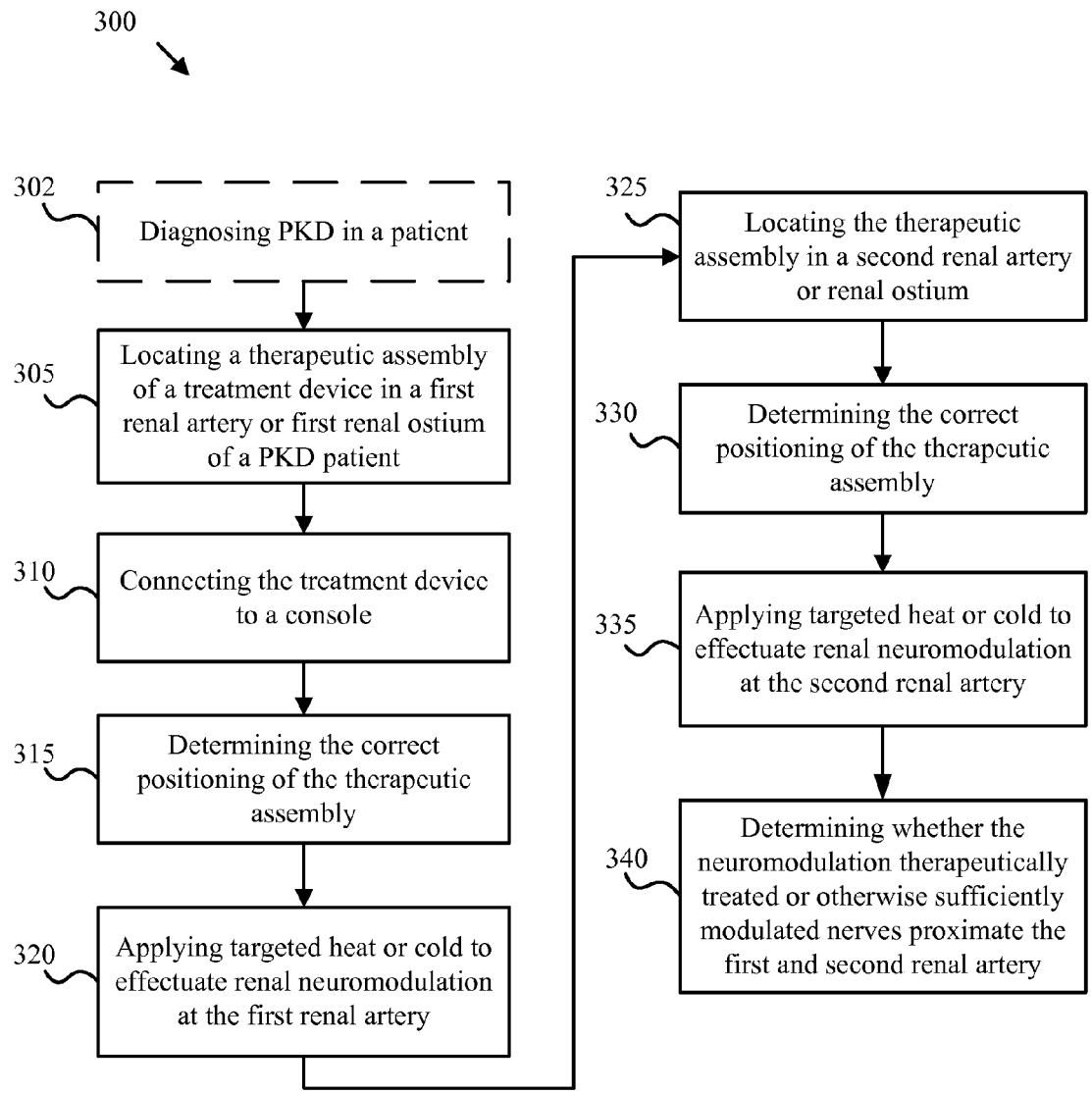
FIG. 3 is a block diagram illustrating a method of modulating renal nerves in accordance with an embodiment of the present technology.

FIG. 3 is a block diagram illustrating a method 300 of modulating renal nerves using the system 10 described above with reference to FIGS. 1 and 2. With reference to FIGS. 1-3 together, the method 300 can optionally include diagnosing PKD in a patient (if not yet determined) and/or selecting a suitable candidate PKD patient for performing renal neuromodulation (block 302). The method 300 can include intravascularly locating the neuromodulation assembly 21 in a delivery state (e.g., low-profile configuration) to a first target site in or near a first renal blood vessel (e.g., first renal artery) or first renal ostium (block 305). The treatment device 12 and/or portions thereof (e.g., the neuromodulation assembly 21) can be inserted into a guide catheter or sheath to facilitate intravascular delivery of the neuromodulation assembly 21. In certain embodiments, for example, the treatment device 12 can be configured to fit within an 8 Fr guide catheter or smaller (e.g., 7 Fr, 6 Fr, etc.) to access small peripheral vessels. A guide wire (not shown) can be used to manipulate and enhance control of the shaft 16 and the neuromodulation assembly 21 (e.g., in an over-the-wire or a rapid-exchange configuration). In some embodiments, radiopaque markers and/or markings on the treatment device 12 and/or the guide wire can facilitate placement of the neuromodulation assembly 21 at the first target site (e.g., a first renal artery or first renal ostium of a PKD patient). In some embodiments, a contrast material can be delivered distally beyond the neuromodulation assembly 21, and fluoroscopy and/or other suitable imaging techniques can be used to aid in placement of the neuromodulation assembly 21 at the first target site.

The method 300 can further include connecting the treatment device 12 to the console 26 (block 310), and determining whether the neuromodulation assembly 21 is in the correct position at the target site and/or whether the neuromodulation assembly electrodes (or cryotherapy balloon) is functioning properly (block 315). Once the neuromodulation assembly 21 is properly located at the first target site and no malfunctions are detected, the console 26 can be manipulated to initiate application of an energy field to the target site to cause electrically-induced and/or thermally-induced partial or full denervation of the kidney (e.g., using electrodes or cryotherapeutic devices). Accordingly, heating and/or cooling of the neuromodulation assembly 21 causes modulation of renal nerves at the first target site to cause partial or full denervation of the kidney associated with the first target site (block 320).

In a specific example, the treatment device 12 can be a cryogenic device and cryogenic cooling can be applied for one or more cycles (e.g., for 30 second increments, 60 second increments, 90 second increments, etc.) in one or more locations along the circumference and/or length of the first renal artery or first renal ostium. The cooling cycles can be, for example, fixed periods or can be fully or partially dependent on detected temperatures (e.g., temperatures detected by a thermocouple (not shown) of the cooling assembly 130). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 21 can then be located at a second target site in or near a second renal blood vessel (e.g., second renal artery) or second renal ostium (block 325), and correct positioning of the assembly 21 can be determined (block 330). In selected embodiments, a contrast material can be delivered distally beyond the neuromodulation assembly 21 and fluoroscopy and/or other suitable imaging techniques can be used to locate the second renal artery. The method 300 continues by applying targeted heat or cold to effectuate renal neuromodulation at the second target site to cause partial or full denervation of the kidney associated with the second target site (block 335).

After providing the therapeutically-effective neuromodulation energy (e.g., cryogenic cooling, RF energy, ultrasound energy, etc.), the method 300 may also include determining whether the neuromodulation therapeutically treated the patient for PKD or otherwise sufficiently modulated nerves or other neural structures proximate the first and second target sites (block 340). For example, the process of determining whether the neuromodulation therapeutically treated the nerves can include determining whether nerves were sufficiently denervated or otherwise disrupted to reduce, suppress, inhibit, block or otherwise affect the afferent and/or efferent renal signals. In a further embodiment, PKD patient assessment could be performed at time intervals (e.g., 1 month, 3 months, 6 months, 12 months) following neuromodulation treatment. For example, the PKD patient can be assessed for measurements of perceived pain, blood pressure control, imaging-based measurements of cyst size and number, markers of renal injury (e.g., serum BUN levels, serum creatinine levels, serum cystatin C levels, proteinuria levels, and NGAL and Kim-1 levels), and measures of sympathetic activity (e.g., MSNA, renal and/or total body spillover, plasma norepinephrine levels, and heart rate variability).

In other embodiments, various steps in the method 300 can be modified, omitted, and/or additional steps may be added. In further embodiments, the method 300 can have a delay between applying therapeutically-effective neuromodulation energy to a first target site at or near a first renal artery or first renal ostium and applying therapeutically-effective neuromodulation energy to a second target site at or near a second renal artery or second renal ostium. For example, neuromodulation of the first renal artery can take place at a first treatment session, and neuromodulation of the second renal artery can take place a second treatment session at a later time.

V. Pertinent Anatomy and Physiology

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal neuromodulation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The SNS is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

1. The Sympathetic Chain

Figure 4:
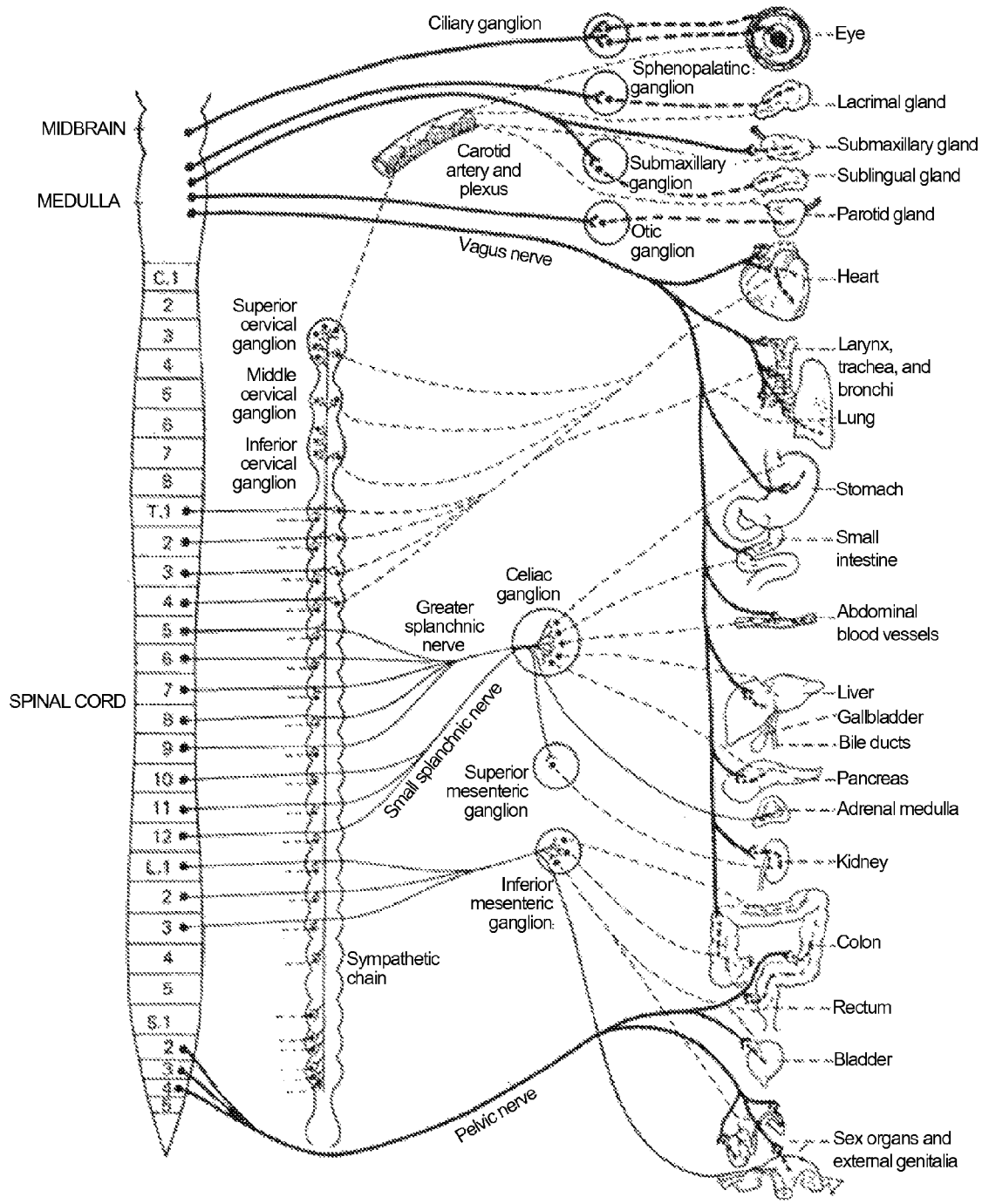
FIG. 4 is a conceptual illustration of the sympathetic nervous system (SNS) and how the brain communicates with the body via the SNS.

As shown in FIG. 4, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 5:
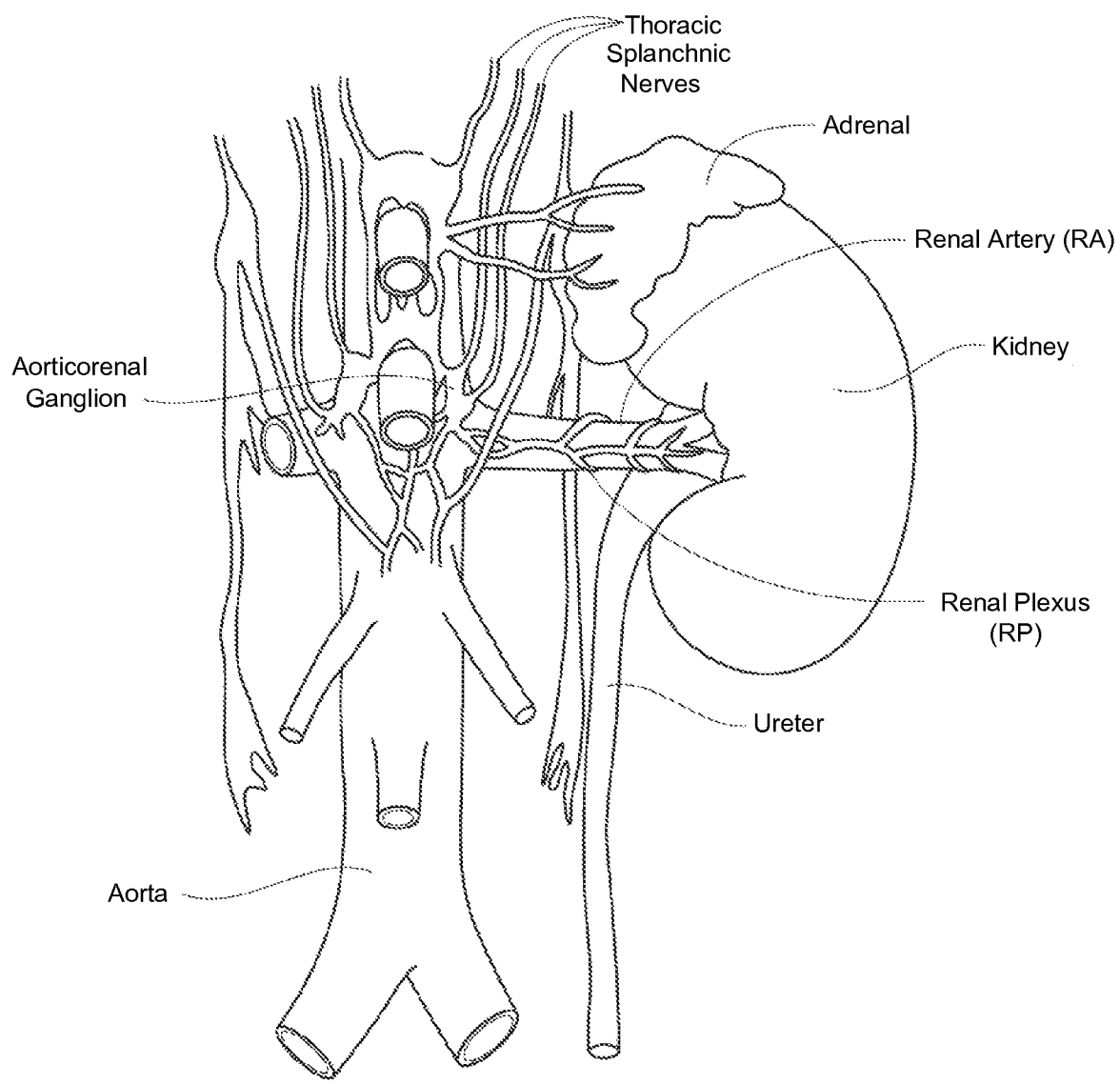
FIG. 5 is an enlarged anatomic view of nerves of a left kidney to form the renal plexus surrounding the left renal artery.

As FIG. 5 shows, the kidney is innervated by the renal plexus RP, which is intimately associated with the renal artery RA. The renal plexus RP is an autonomic plexus that surrounds the renal artery RA and is embedded within the adventitia of the renal artery RA. The renal plexus RP extends along the renal artery RA until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the SNS may accelerate heart rate; widen bronchial passages; decrease motility (movement) of the large intestine; constrict blood vessels; increase peristalsis in the esophagus; cause pupil dilation, cause piloerection (i.e., goose bumps), cause perspiration (i.e., sweating), and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing overactivity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine (NE) from the kidneys to plasma revealed increased renal NE spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced SNS overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end-stage renal disease are characterized by heightened sympathetic nervous activation. In patients with end-stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic overactivity, such as hypertension, left ventricular hypertrophy, ventricular arrhythmias, sudden cardiac death, insulin resistance, diabetes, and metabolic syndrome.

(i) Renal Sympathetic Efferent Nerve Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 6A:
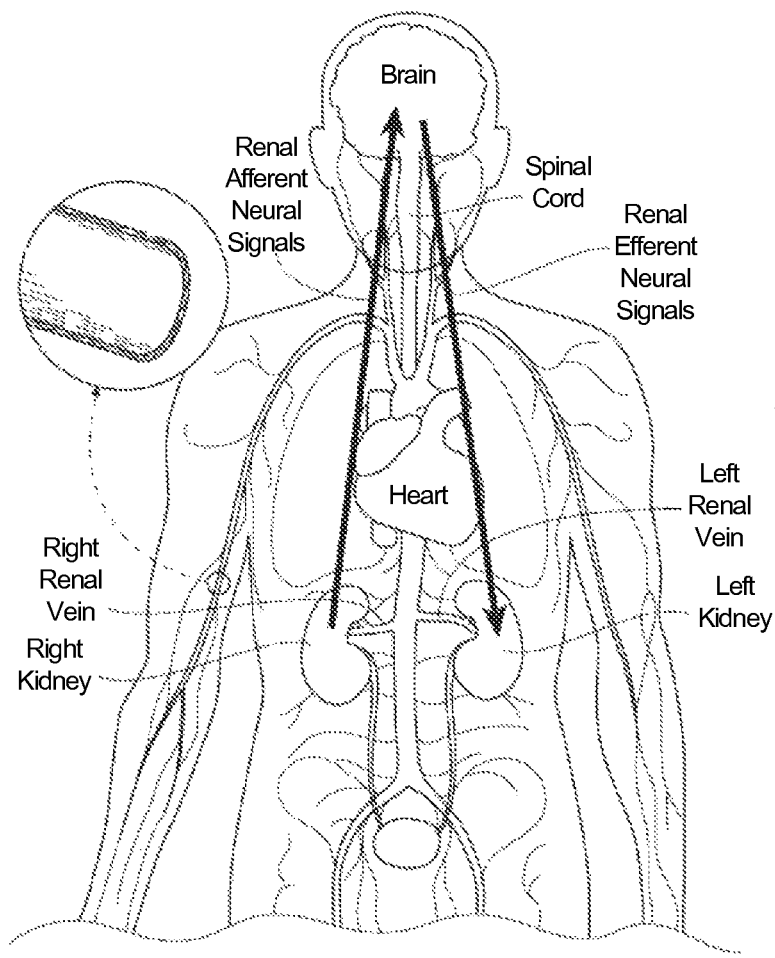
FIGS. 6A and 6B are anatomic and conceptual views, respectively, of a human body depicting neural efferent and afferent communication between the brain and kidneys.
Figure 6B:
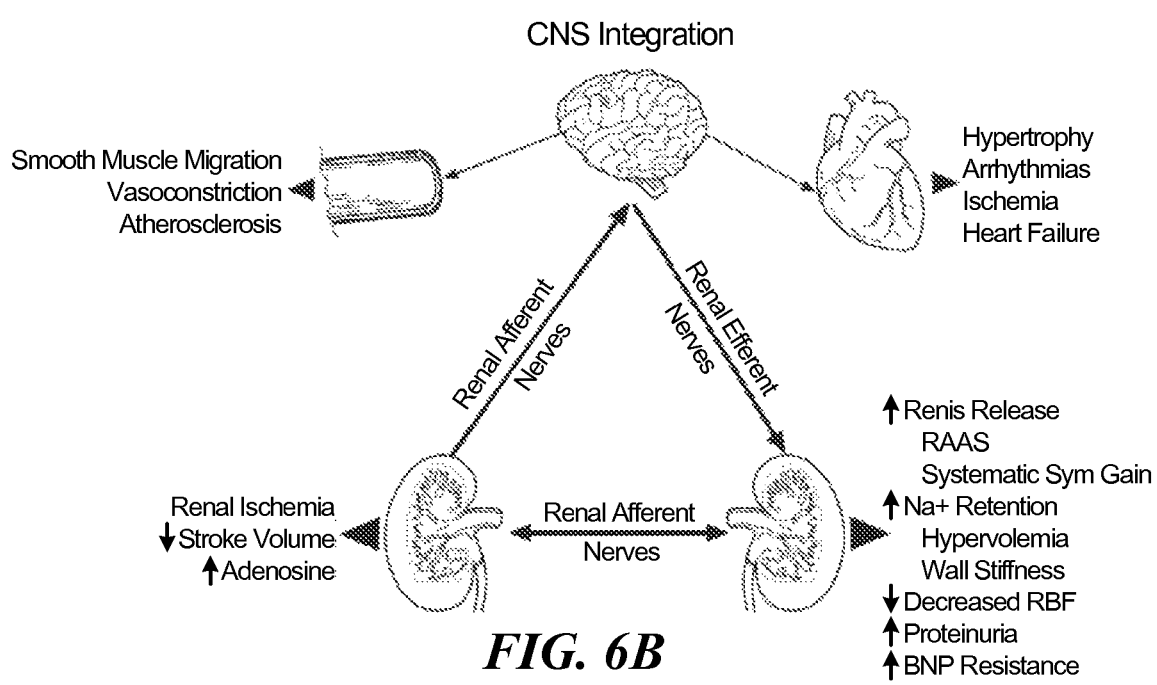

The kidneys communicate with integral structures in the CNS via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 6B and 6B, this afferent communication might be from the kidney to the brain or might be from one kidney to the other kidney (via the CNS). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and renal blood flow, and (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Neuromodulation

As provided above, renal neuromodulation is likely to be valuable in the treatment of several clinical conditions characterized by increased overall and particularly renal sympathetic activity such as hypertension, metabolic syndrome, insulin resistance, diabetes, left ventricular hypertrophy, chronic end-stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 4. For example, as previously discussed, a reduction in central sympathetic drive may reduce the insulin resistance that afflicts people with metabolic syndrome and Type II diabetes. Additionally, patients with osteoporosis are also sympathetically activated and might also benefit from the down regulation of sympathetic drive that accompanies renal denervation.

C. Achieving Intravascular Access to the Renal Artery

Figure 7A:
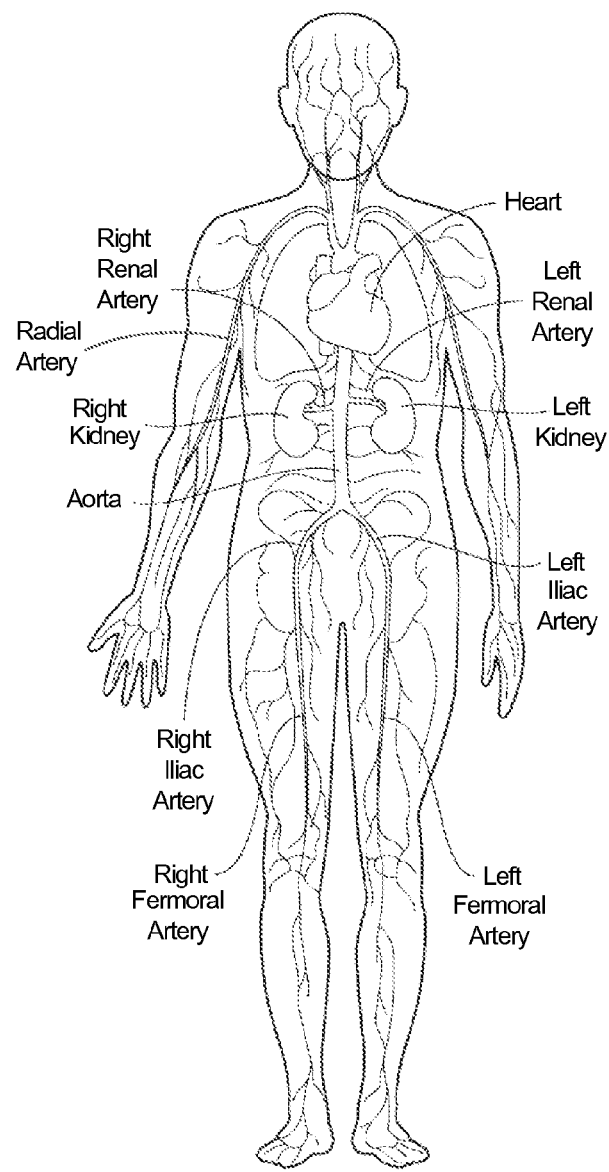
FIGS. 7A and 7B are anatomic views of the arterial vasculature and venous vasculature, respectively, of a human.

In accordance with the present technology, neuromodulation of a left and/or right renal plexus RP, which is intimately associated with a left and/or right renal artery, may be achieved through intravascular access. As FIG. 7A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 7B:
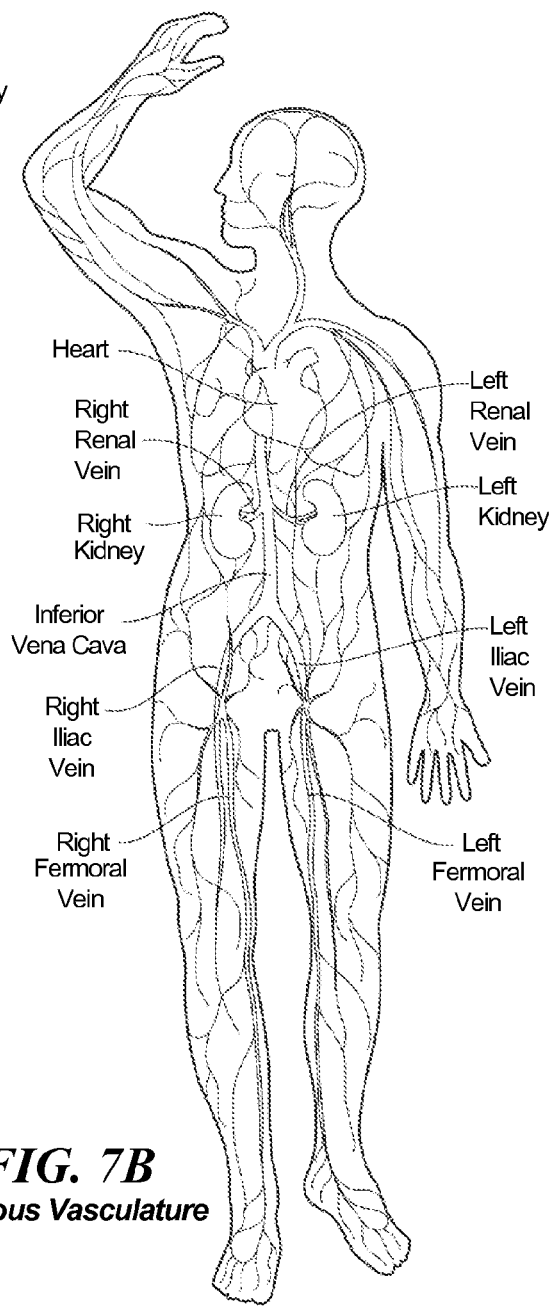

As FIG. 7B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with embodiments of the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as polycystic kidney disease, hypertension, other chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access can account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within a renal artery RA, as well as tortuosity of the artery. Furthermore, establishing consistent contact can be complicated by patient movement, respiration, and/or the cardiac cycle because these factors may cause significant movement of the renal artery RA relative to the aorta, and the cardiac cycle may transiently distend the renal artery RA (i.e., cause the wall of the artery to pulse).

After accessing a renal artery and facilitating stable contact between neuromodulatory apparatus and a luminal surface of the artery, nerves in and around the adventitia of the artery can be modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy can be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery RA can be applied carefully. Accordingly, the complex fluid mechanics and thermodynamic conditions present in the renal artery during treatment, particularly those that may impact heat transfer dynamics at the treatment site, may be important in applying energy (e.g., hearting thermal energy) and/or removing heat from the tissue (e.g., cooling thermal conditions) from within the renal artery.

The neuromodulatory apparatus can also be configured to allow for adjustable positioning and repositioning of an energy delivery element or a cryotherapeutic device, within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the cryotherapeutic devices or energy delivery elements and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the takeoff angle of a renal artery relative to the aorta. These properties will be discussed in greater detail with respect to the renal arteries. However, depending on the apparatus, systems, and methods utilized to achieve renal neuromodulation, such properties of the renal arteries also may guide and/or constrain design characteristics.

As noted above, an apparatus positioned within a renal artery can conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite intima-media thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment can be important to reach the target neural fibers, the treatment typically is not too deep (e.g., the treatment can be less than about 5 mm from inner wall of the renal artery) so as to avoid non-target tissue and anatomical structures such as the renal vein.

An additional property of the renal artery that may be of interest is the degree of renal motion relative to the aorta, induced by respiration and/or blood flow pulsatility. A patient's kidney, which is located at the distal end of the renal artery, may move as much as four inches cranially with respiratory excursion. This may impart significant motion to the renal artery connecting the aorta and the kidney. Accordingly, the neuromodulatory apparatus can have a unique balance of stiffness and flexibility to maintain contact between a cryo-applicator or another thermal treatment element and the vessel wall during cycles of respiration. Furthermore, the takeoff angle between the renal artery and the aorta may vary significantly between patients, and also may vary dynamically within a patient, e.g., due to kidney motion. The takeoff angle generally may be in a range of about 30°-135°.

VI. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. For example, in additional embodiments, the system 10 may include a treatment device configured to deliver therapeutic energy to the patient from an external location outside the patient's body, i.e., without direct or close contact to the target site. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method, comprising:
    percutaneously introducing a neuromodulation assembly at a distal portion of a treatment device proximate to neural fibers innervating a kidney of a human patient diagnosed with autosomal dominant polycystic kidney disease (ADPKD);
    at least partially disrupting function of the neural fibers by applying thermal energy to the neural fibers via the neuromodulation assembly; and
    removing the neuromodulation assembly from the patient after treatment;
    wherein at least partial disruption of the function of the neural fibers reduces a size of the kidney in the patient diagnosed with ADPKD.

2. The method of claim 1 wherein at least partially disrupting function of the neural fibers comprises reducing central sympathetic drive in the patient in a manner that therapeutically treats the ADPKD of the patient.

3. The method of claim 2 wherein reducing central sympathetic drive in the patient includes at least one of reducing muscle sympathetic nerve activity or reducing whole body norepinephrine spillover in the patient.

4. The method of claim 1 wherein introducing a neuromodulation assembly proximate to neural fibers of the patient comprises positioning the neuromodulation assembly within a renal artery of the patient.

5. The method of claim 1 wherein introducing a neuromodulation assembly proximate to neural fibers of the patient comprises positioning the neuromodulation assembly within a renal vein of the patient.

6. The method of claim 1, further comprising administering one or more pharmaceutical drugs to the patient, wherein the pharmaceutical drugs are selected from the group consisting of antihypertensive drugs, pain drugs, vasopressin inhibitors and mTOR inhibitors.

7. The method of claim 1 wherein at least partial disruption of the function of the neural fibers further reduces a level of fluid retention in one or more kidney cysts of the patient diagnosed with ADPKD.

8. The method of claim 1 wherein at least partial disruption of the function of the neural fibers further reduces a severity and/or frequency of pain in the patient diagnosed with ADPKD.

9. The method of claim 1 wherein at least partial disruption of the function of the neural fibers further slows a rate of decline in glomerular filtration rate of the patient diagnosed with ADPKD.

10. The method of claim 1 wherein at least partial disruption of the function of the neural fibers further results in reducing expansion of, maintaining the size of, or reducing the size of a liver cyst in the patient diagnosed with ADPKD.

11. The method of claim 1 wherein at least partial disruption of the function of the neural fibers further results in reducing expansion of, maintaining the size of, or reducing the size of a pancreatic cyst in the patient diagnosed with ADPKD.

12. The method of claim 1 wherein at least partial disruption of the function of the neural fibers further results in preventing or delaying onset of end-stage renal disease in the patient diagnosed with ADPKD.

13. The method of claim 1 wherein the size of the kidney reduces at least about 5% within about 3 months to about 12 months after at least partial disruption of the function of the neural fibers in the patient diagnosed with ADPKD.

14. A method for treating a human patient having an autosomal dominant polycystic kidney disease (ADPKD)-associated genetic mutation in at least one of the PKD-1, PKD-2, PKD-3 gene alleles, the method comprising:
    positioning an energy delivery element of a renal denervation catheter within a renal blood vessel of the patient and adjacent to post-ganglionic neural fibers that innervate a kidney of the patient; and
    at least partially ablating a renal nerve of the patient via the energy delivery element,
    wherein at least partially ablating the renal nerve results in at least one of slowing a rate of kidney cyst formation, preventing kidney cyst formation, and slowing a rate of kidney enlargement in the patient having the ADPKD-associated genetic mutation in at least one of the PKD-1, PKD-2, PKD-3 gene alleles.

15. The method of claim 14 wherein the patient has one or more kidney cysts, and wherein at least partially ablating the renal nerve further results in a therapeutically beneficial reduction in one or more of blood pressure, kidney cyst size and perceived pain of the patient.

16. The method of claim 14 wherein at least partially ablating the renal nerve further results in preventing or delaying onset of end-stage renal disease in the patient.

17. The method of claim 14 wherein at least partially ablating the renal nerve further results in slowing a decline in a glomerular filtration rate of the patient.

18. The method of claim 14 wherein the patient has elevated blood pressure, and wherein at least partially ablating the renal nerve results in improved blood pressure control.

19. The method of claim 14 wherein at least partially ablating the renal nerve further results in at least one of slowing a rate of cyst formation, preventing cyst formation and slowing a rate of organ enlargement in the liver and/or the pancreas in the patient.

* * * * *